(12) United States Patent
Bakaletz et al.

(10) Patent No.: US 7,811,590 B2
(45) Date of Patent: Oct. 12, 2010

(54) HAEMOPHILUS INFLUENZAE OUTER MEMBRANE PROTEIN AND USE THEREOF IN VACCINATION

(75) Inventors: Lauren O. Bakaletz, Columbus, OH (US); Francois-Xavier Jacques Berthet, Barcelona (ES); Philippe Denoel, Rixensart (BE); Jan Poolman, Rixensart (BE); Joelle Thonnard, Rixensart (BE)

(73) Assignees: The Ohio State University Research Foundation, Columbus, OH (US); GlaxoSmithKline, King of Prussia, PA (US)

( * ) Notice: Subject to any disclaimer, the term of this patent is extended or adjusted under 35 U.S.C. 154(b) by 71 days.

(21) Appl. No.: 11/960,883

(22) Filed: Dec. 20, 2007

(65) Prior Publication Data

US 2009/0175912 A1    Jul. 9, 2009

Related U.S. Application Data

(63) Continuation of application No. 11/336,327, filed on Jan. 20, 2006, now abandoned, which is a continuation of application No. 10/203,942, filed as application No. PCT/EP01/01556 on Feb. 13, 2001, now abandoned.

(30) Foreign Application Priority Data

Feb. 15, 2000    (GB) ................................. 0003502.2

(51) Int. Cl.
*A61K 39/102*    (2006.01)
(52) U.S. Cl. .............. 424/256.1; 424/251.1; 424/185.1; 424/190.1; 424/200.1; 530/350

(58) Field of Classification Search ....................... None
See application file for complete search history.

(56) References Cited

FOREIGN PATENT DOCUMENTS

WO    WO 99/64067    12/1999

OTHER PUBLICATIONS

Greenspan et al (Nature Biotechnology 7: 936-937, 1999).*
Chothia et al (The EMBO Journal, 1986, 5/4:823-26).*
Bakaletz, et al., "Protection Against Development of Otitis Media Induced by Nontypeable *Haemophilus influenzae* by Both Active and Passive Immunization in a Chinchilla Model of Virus-Bacterium Superinfection". *Infection and Immunity*, 67(6): 2746-2762 (1999).
Webb, et al., "Secondary Structure and Molecular Analysis of Interstrain Variability in the P5 Outer-Membrane Protein of Non-Typeable *Haemophilus influenzae* Isolated from Diverse Anatomical Sites". *Journal of Medical Microbiology*, 47(12): 1059-1067 (1998).
Munson et al. *Infect. Immun.*, 61(9): 4017-4020 (1993).
Mikayama et al. *Proc. Natl. Acad. Sci. USA*, 90: 10056-10060 (1993).
Rudinger et al. *Peptide Hormones Biol. Council*, 1-7 (1976).

* cited by examiner

*Primary Examiner*—Jennifer E Graser
(74) *Attorney, Agent, or Firm*—Calfee, Halter & Griswold LLP

(57) ABSTRACT

This invention relates to recombinant bacterial outer membrane proteins comprising one or more LB1(f) peptides from surface-exposed loop 3 of MOMP P5 of non-typeable *H. influenzae*. Polynucleotides encoding these recombinant proteins are also covered. The invention also relates to a method of isolating the recombinant proteins and a vaccine composition for use in the treatment of *Haemophilus influenzae* infection.

10 Claims, 2 Drawing Sheets

```
                                        <-    Loop 1
  1    MKKTAIALVV AGLAAASVAQ AAPQENTFYA GVKAGQASFH DGLRALAREY ->                               <-   Loop 2  ->
 51    KVGYHRNSFT YGVFGGYQIL NQNNLGLAVE LGYDDFGRAK GREKGKTVVK <-   Loop 3  ->
101    HTNHGTHLSS KGSYEVLEGL DVYGKAGVAL VRSDYKLYNE NSSTLKKLGE <-   Loop 4
151    HHRARASGLF AVGAEYAVLP ELAVRLEYQW LTRVGKYRPQ DKPNTALNYN

->
201    PWIGSINAGI SYRFGQGAAP VVAAPEVVSK TFSLNSDVTF AFGKANLKPQ

251    AQATLDSIYG EMSQVKSAKV AVAGYTDRIG SDAFNVKLSQ ERADSVANYF

301    VAKGVAADAI SATGYGKANP VTGATCDQVK GRKALIACFA PDRRVEIAVN

351    GTK
```

```
                                                        <-      Loop 1
1       MKKTAIALVV  AGLAAASVAQ  AAPQENTFYA  GVKAGQASFH  DGLRALAREY ->                                          <-  Loop 2  ->
51      KVGYHRNSFT  YGVFGGYQIL  NQNNLGLAVE  LGYDDFGRAK  GREKGKTVVK <-  Loop 3  ->
101     HTNHGTHLSS  KGSYEVLEGL  DVYGKAGVAL  VRSDYKLYNE  NSSTLKKLGE <-      Loop 4
151     HHRARASGLF  AVGAEYAVLP  ELAVRLEYQW  LTRVGKYRPQ  DKPNTALNYN

->
201     PWIGSINAGI  SYRFGQGAAP  VVAAPEVVSK  TFSLNSDVTF  AFGKANLKPQ

251     AQATLDSIYG  EMSQVKSAKV  AVAGYTDRIG  SDAFNVKLSQ  ERADSVANYF

301     VAKGVAADAI  SATGYGKANP  VTGATCDQVK  GRKALIACFA  PDRRVEIAVN

351     GTK
```

Figure 1 (SEQ ID NO: 9)

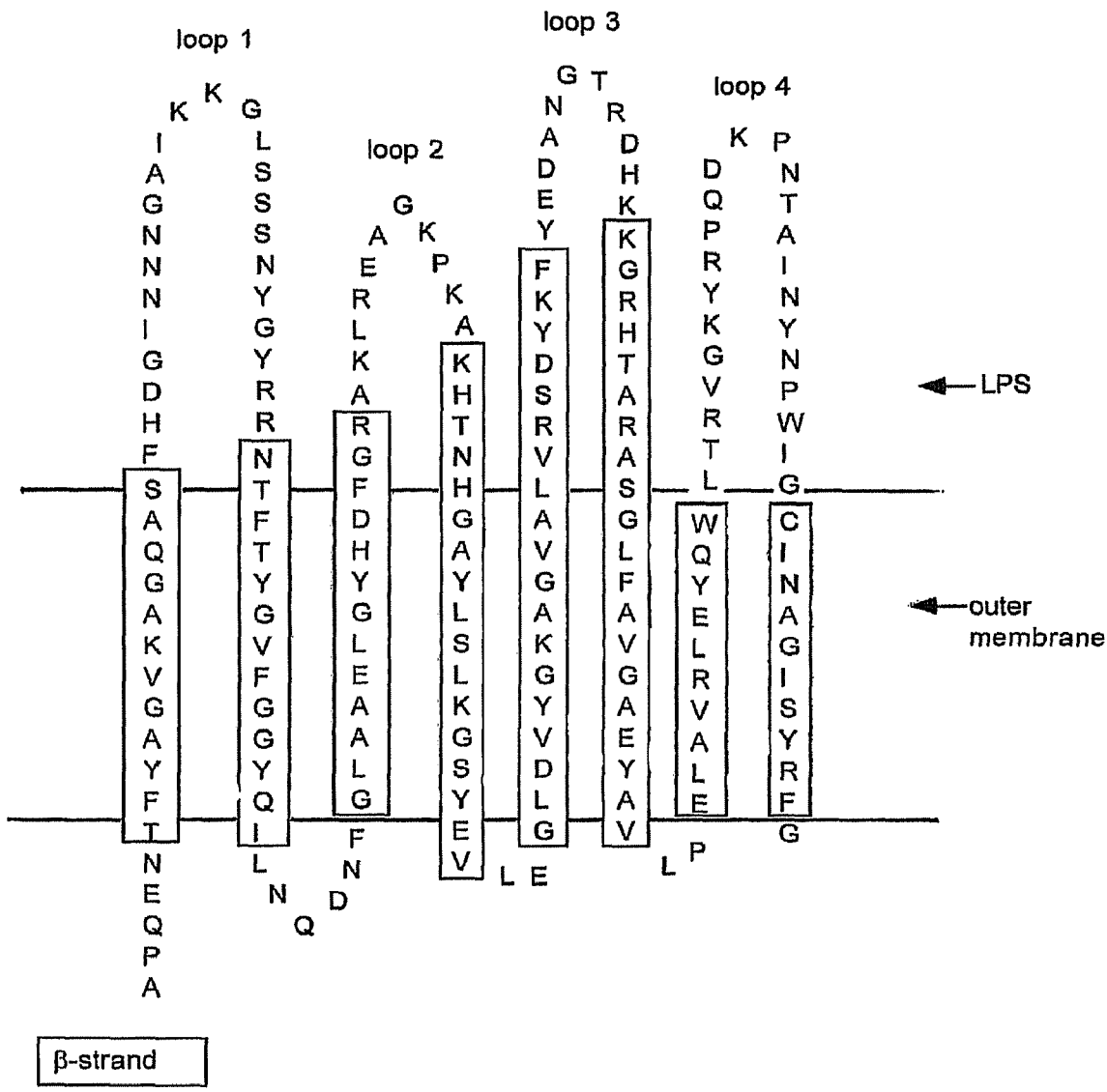
Figure 2 (SEQ ID NO: 10)

HAEMOPHILUS INFLUENZAE OUTER MEMBRANE PROTEIN AND USE THEREOF IN VACCINATION

This application is a continuation of application Ser. No. 11/336,327, filed Jan. 20, 2006, now abandoned, which is a continuation of application Ser. No. 10/203,942, filed Oct. 21, 2002, now abandoned, which is a 371 national stage entry of International Application No. PCT/EP01/01556, filed Feb. 13, 2001, which claims priority of Great Britain Application No. 0003502.2, filed Feb. 12, 2000.

FIELD OF INVENTION

This invention relates to newly identified *Haemophilus influenzae* chimeric proteins and polynucleotides encoding these proteins. The invention also relates to a method of isolating the chimeric proteins and a vaccine composition for use in the treatment of *Haemophilus influenzae* infection.

BACKGROUND OF THE INVENTION

*Haemophilus influenzae* (Hi) is a gram-negative coccobacillus and a strict human commensal. Strains of Hi are either encapsulated in a polysaccharide capsule or are non-encapsulated and are accordingly classified into typeable (encapsulated) and non-typeable (non-encapsulated) strains.

Encapsulated pathogenic strains of Hi cause mainly, but not exclusively, invasive disease in children under six years of age. *Haemophilus influenzae* type b (Hib), for example, is a major cause of meningitis and other invasive infections in children. Effective vaccines exist against Hib infections, and are based on producing antibodies to the polysaccharide capsule, and are therefore ineffective against non-typeable *Haemophilus influenzae* (ntHi).

Non-typeable *Haemophilus influenzae* (ntHi) represents the majority of the colonising strains and, although rarely invasive, are responsible for a significant proportion of mucosal disease including otitis media, sinusitis, chronic conjunctivitis and chronic or exacerbation of lower respiratory tract infections. Currently, approximately 30%, and as much as 62% of ntHi are resistant to penicillins. Carriage is estimated at 44% in children and approximately 5% in adults, and can persist for months. Neither the pathogenic mechanisms nor the host immunological response has been fully defined for otitis media caused by ntHi.

Otitis media is a common disease in children less than 2 years of age. It is defined by the presence of fluid in the middle ear accompanied by a sign of acute local or systemic illness. Acute signs include ear pain, ear drainage, hearing loss whereas systemic signs include fever, lethargy, irritability, anorexia, vomiting or diarrhoea. *Streptococcus pneumoniae* and non-typeable *Haemophilus influenzae* (nthi) are the most predominant bacteria that cause the condition, accounting for 25-50%, and 15-30% of the species cultured, respectively. *Moraxella catarrhalis* is another common cause of the disease. In addition, ntHi is responsible for 53% of recurrent otitis media. Approximately 60% and 80% of children have at least one episode of the disease by 1 and 3 years of age respectively (the peak being around 10 months).

There is evidence that protective immunity does exist for ntHi, however antigenic drift in the epitopes naturally involved (outer-membrane proteins P2, P4, P6) plays a major role in the ability of ntHi to evade the immune defence of the host.

There is therefore a need for additional effective vaccines against *Haemophilus influenzae*, and particularly for vaccines against non-typeable *Haemophilus influenzae* which is not affected by the currently available Hi polysaccharide vaccines.

Major Outer Membrane Protein (MOMP) P5 is a heat-modifiable outer membrane protein of *H. influenzae*. P5 may play a role in ntHi pathogenesis as an adhesin by binding to respiratory mucin or to RSV-infected respiratory epithelial cells (Reddy et al. (1996) Infect. Immun. 64:1477-1479; Jiang et al. (1999) Infect. Immun. 65:1351-1356). This binding activity could be mediated by surface exposed regions of the protein. The protein has been shown to be a protective antigen in various models.

There are conflicting reports with regards to the structure of this protein. Although it has been reported that the protein adopts a fimbriae structure composed of assembled coiled coils, this is contradictory to the similarity of sequences observed between P5 and *E. coli* OmpA which is an eight-stranded β-barrel-forming protein with four surface exposed loops (Munson et al. (1993) Infect Immun. 61:4017-4020).

During persistent infections by ntHi in patients with chronic bronchitis, ntHi variant strains with alterations in their OMP P5 sequences appear. Also, isolates from different anatomical sites display such variability. However this variability is mostly limited to 4 regions. These regions correspond to the regions predicted as surface exposed and as a consequence that could be exposed to the immune system pressure. Upon infection, the appearance of P5 strain variants could be an escape mechanism for ntHi or could enable the bacteria to colonise different anatomical sites (Webb and Cripps (1998) J. Med. Microbiol. 47:1059-1067; Duim et al. (1997) Infect. Immun. 65:1351-1356). Even so, it has been shown that mice anti-P5 purified antibodies were bactericidal for the homologous and a few heterologous ntHi strains (Quigley-Reape et al. (1995) Abstr. E70, p 239. In Abstracts of the 95$^{th}$ ASM general meeting 1995).

LB1(f) is a 19 amino-acid peptide derived from the sequence of MOMP P5 from strain ntHi1128 (occupying the region Arg117 to Gly135). This peptide was defined as being the third exposed loop of P5, and as being a potential B cell epitope, by analysis of the primary sequence of P5. Immunising animals with chimeric fimbrin peptides (called LB1 peptides), comprising: the LB1(f) peptide; a linker peptide; and a T cell epitope, induces a protective immune response to the MOMP P5 and reduces the colonization of ntHi in animals subsequently exposed to ntHi (see U.S. Pat. No. 5,843,464).

The problem with using protein antigens from only one strain of *H. influenzae* in a vaccine is that protection conferred tends to be largely restricted to homologous challenge [Bakaletz et al. (1997) Vaccine 15:955-961; Haase et al. (1991) Infect. Immun. 59:1278-1284; Sirakova et al. (1994) Infect. Immun. 62:2002-2020]. The antigenic diversity of the ntHi Outer Membrane Proteins, means that development of a broadly effective vaccine against a group of organisms as heterogeneous as ntHi will require a new strategy.

WO 99/64067 discloses a more effective use of the LB1(f) peptide as a vaccine against a broad spectrum of heterologous *Haemophilus influenzae* strains that express the MOMP P5 (or naturally occurring variants of the protein). This involved the identification of the 3 antigenic groups of LB1(f) peptides that define the population of LB1(f) peptides present in heterologous ntHi MOMP P5 proteins, Chimeras of these peptides were suggested as a immunogen in order to obtain a protective immune response against a large variety of ntHi strains.

A problem that exists is that in order for these peptides to work optimally as effective immunogens, they must be able to generate antibodies which recognise and bind to the epitopes in their native structure.

Accordingly, the present invention relates to a method of increasing the effectiveness of the LB1(f) peptides by inserting them into surface exposed loops of other outer membrane proteins, or, preferably, back into MOMP P5 itself such that the epitopes may be better recognised in their native conformation by the immune system. Such recombinant outer membrane proteins of the invention have one or more of the following advantages: the context of the important LB1(f) B epitopes is in a favourable context (with a constrained structure) for better immune recognition and immunogenicity; protective LB1(f) epitopes may replace hypervariable, non-protective epitopes from the outer membrane protein to focus the immune response to the protective LB1(f) peptides; the recombinant, modified outer membrane protein helps to provides a better protective immune response against a wide range of ntHi strains.

SUMMARY OF THE INVENTION

It is an object of the present invention to provide recombinant outer membrane protein comprising one or more surface exposed loops, wherein one or more native surface-exposed loops of the protein (those loops present on the native, wild-type protein) have been replaced with one or more modified loops comprising an amino-acid sequence selected from the group consisting of: SEQ. ID NO: 1-8 (each comprising an LB1(f) peptide), or antigenically related variants of said sequences which have an identity of at least 75% and are capable of immunologically mimicking a corresponding antigenic determinant site of the MOMP P5 of ntHi.

Preferably, the recombinant outer membrane protein is derived from a native (wild-type) outer membrane protein which is from non-typeable *Haemophilus influenzae* or *Moraxella catarrhalis*. This is advantageous in terms of providing further protective antigens against *H. influenzae* in a single molecule, or for providing a single molecule which can provide protection to a host against 2 causes of otitis media: ntHi and *Moraxella catarrhalis*.

In a preferred embodiment recombinant, modified MOMP P5 protein is provided. Such proteins are advantageous in that they already contain an LB1(f) peptide in the third loop in a native, protective conformation (which preferably should be unchanged). Of course, in this embodiment where only one (single) native loop is modified by replacing it with a loop comprising an LB1(f) peptide, the invention does not cover embodiments where the single native loop is the third loop of the native OMP (which already comprises an LB1 (f) peptide).

It is a further object to provide polynucleotides encoding such proteins. The invention also relates to a method of isolating the proteins, and to a vaccine composition for use in the treatment of *Haemophilus influenzae* infection, or otitis media.

The invention may be more fully understood by reference to the following drawings and detailed description.

BRIEF DESCRIPTION OF THE DRAWINGS

FIG. 1: The amino acid sequence of MOMP P5, SEQ ID NO: 9. A conservative assessment of the position of the 4 external loops is indicated. Loop 3 corresponds to a Group 2b LB1(f) peptide.

FIG. 2: Topology model of the outer-membrane integrated part of MOMP P5 from nthi 1128 strain (loop 3 corresponds to a Group 1 LB1(f) peptide). Looking from left to right along the outer surface of the outer membrane, the A, F, D, G, A, G, W and C boundary residues are likely to be associated with the outer membrane, and therefore a liberal (and more accurate) assessment of the position of the 4 external loops are the 4 amino acid sequences outside, but not including, the aforementioned boundary residues (SEQ ID NO: 10).

DETAILED DESCRIPTION OF THE PREFERRED EMBODIMENT

Outer Membrane Proteins of the Invention

The recombinant outer membrane protein of the invention may be derived from any native (wild-type), bacterial outer membrane protein that has at least one surface-exposed loop. Preferably said native outer membrane protein should be from a Gram-negative bacterium, most preferably from *Haemophilus influenzae* (preferably non-typeable *H. influenzae*), or *Moraxella catarrhalis*.

The DNA sequences of various *H. influenzae* outer membrane proteins for the purpose of this invention are known and described in Genbank, or in WO 96/33276. Information in such disclosures will allow a skilled person to clone the native gene from ntHi. Preferred native ntHi outer membrane proteins for the purposes of this invention are: P1 (Bolduc et al. 2000 Infect. Immun. 68:4505); P2 (Sikkema and Murphy (1992) Infect. Immun. 60:5204; Kyungcheol and Murphy (1997) Infect. Immun. 65:150; Neary et al. (1999) 99th Gen. meeting of the ASM, Poster E-10; Duim et al. (1996) Infect. Immun. 64:4673); P4; P5 (WO 94/26304); D15 (WO 94/12641); Omp26 (WO 97/01638); HMW[1 & 2] (Barenkamp and Leininger (1992) Infect. Immun. 60:1302; Loosmore et al. WO00/20609; Loosmore et al. WO00/35477; Barenkamp WO9736914A); HMW[3 & 4] (Barenkamp et al. WO9736914-A1); HxuA (Cope et al. (1994) Mol. Microbiol. 13:863; Hanson et al. (1992) PNAS 89:1973.); ..HgpA (Jin et al. (1996) Infect. Immnu. 64:3134; Hanson et al. (1992) Infect. Immun. 60:2257; Jin et al. (1999) Microbiology 145: 905.); TbpA (Loosmore et al U.S. Pat. No. 6,008,326; Loosmore et al. U.S. Pat. No. 6,015,688); Hsf/Hia (Loosmore et al WO 00/55191; Barenkamp and StGemeIII (1996) Mol. Microbiol. 19:1215.); Hap (StGeme et al. (1994) Mol. Microbiol. 14:217.); Iomp1681 (GB 0025998.6); D15b (WO 00/47737); HasR (WO 00/50599); YadA; IgAprotease; and VirG (GB 0026002.6).

The DNA sequences of various *Moraxella calarrhalis* outer membrane proteins for the purpose of this invention are known and described in Genbank, or in WO 00/78968. Information in such disclosures will allow a skilled person to clone the native gene from *Moraxella catarrhalis*. Preferred native *Moraxella catarrhalis* outer membrane proteins for the purposes of this invention are: OmpA; OmpB1/B2 (Chen et al., WO 98/33814); OmpCD (Hsiao et al. (1995) Microb. Pathog. 19:215.); OmpE (Murphy et al. U.S. Pat. No. 5,948,412); Omp106 (WO 97/41731 & WO 96/34960); TbpA (WO 97/13785 & WO 97/32980); LbpA (WO 98/55606); CopB (Helminen et al. (1993) Infect. Immun. 61:2003-2010); OmplA1(WO 00/15802); D15 (WO 99/63093); D15b (WO 00/52042); PilQ (WO 99/64448); Mip (WO 00/09694); HasR (WO 99/64602); OmpA (WO 00/71724); AperE (GB 9912038.8); OmpF (GB 9912674.0); OmpS (GB 9912705.2); HutA1/A2 (GB 9912838.1/GB 9913354.8);

FHA C (GB 9921693.9); PorA (PCT/EP00/09034); CyaE (GB 9922829.8); UspA1 & UspA2 (WO 93/03761); and Omp21.

Recombinant Outer Membrane Proteins of the Invention

The skilled person is readily able to determine the surface exposed loops of native outer membrane proteins using well-known methodology, and topology models already known for the above outer membrane proteins. Typically a skilled person would determine where these loops are by running secondary structure prediction programs looking for β-strands (secondary structure that traverses the outer membrane for bacterial OMPs). β-strands in OMPs that cross the membrane tend to be approximately 10 amino acids long, and tend to be amphipathic. As OMPs tend to start and end on the inner side of the outer membrane, pairs of β-strands are usually searched for (in total at least 2 β-strands, but sometimes up to 20 or so). Frequently aromatic amino acids delineate the beginning and/or end of such a strand. Surface-exposed loops reside in between pairs of β-strands. Further indications that a surface-exposed loop has been identified is that: a) they tend to be longer than loops on the internal surface of the membrane (5 to 30 or more amino acids versus 2-6 amino acids), and b) they tend to be quite variable when comparing the same sequence in different strains of the same bacterium (whereas the β-strand sequences tend to be conserved). Preferably surface-exposed loops are determined using experimentally tested topology models (or structures) of homologous outer membrane proteins (with amino acid identity of more than 20, 30, 40, 50, 60, 70, 80, or 90%). Experimental tests also exist to determine surface-exposed loops: the loops are the portions of the protein that raise antibodies in a host (and antibodies so collected can be used to determine where on the protein primary sequence the surface epitopes are); and areas of the protein susceptible to being processed by proteases.

For instance, the 4 surface-(externally-) exposed loops of MOMP P5 (of ntHi) are indicated in FIGS. 1 (a conservative topology for a Group 2b LB1(f) MOMP P5) and 2 (a more accurate representation of the topology of the MOMP P5 loops for a Group 1 LB1 (f) MOMP P5), and can be readily determined by the skilled person for other variants of MOMP P5. This is because the outer membrane associated regions (as shown in FIG. 2) are highly conserved amongst all MOMP P5 proteins. Therefore looking from left to right along the outer surface of the outer membrane in FIG. 2, the A, F, D, G, A, G, W and C boundary residues are likely to be associated with the outer membrane, and therefore an accurate assessment of the position of the 4 external loops are the 4 amino acid sequences outside, but not including, the aforementioned boundary residues.

LB1(f) peptides consist of 13 to about 22 amino acids. The peptides fall into 3 main immunological groups: 1, 2 and 3 (group 2 being split into 2 marginally different subgroups: 2a and 2b). A large set of known LB1(f) peptides from the 3 groups (and variants thereof) are disclosed in WO 99/64067 which is hereby incorporated by reference.

A (native) surface-exposed loop is replaced with a modified surface-exposed loop if a wild-type surface loop is altered in any way so as to contain an LB1(f) peptide. The term therefore covers where an LB1(f) peptide is inserted (or placed within) the target loop at any position on the native loop. Preferably the insertion is at the centre point of the loop. Replacement of a loop can be a complete change of sequence of the native loop, or a partial change. A partial change can be of 1, 2, 3, 4, 5 or more amino acids from a loop, and is preferably a continuous sequence of amino acids in the loop. Preferably the entire loop is replaced, or the entire loop but for 1-2 amino acids at either end of the loop. A loop of X amino acids may be replaced with a peptide of X amino acids for the optimal folding of the recombinant outer membrane protein.

The modified loops of the invention should comprise an LB1(f) peptide. These loops are modified in terms of being in a non-native environment in the recombinant outer-membrane protein of the invention (the modified loop may therefore be a wild-type sequence of loop 3 from MOMP P5). As disclosed in WO 99/64067, the groups of LB1 (f) peptides contain a wide variety of immunologically-related variant sequences which have an identity of at least 75% with the representative peptide of the group shown in SEQ ID NO: 1-4. Most preferably, the native surface-exposed loop should be replaced completely with an entire loop 3 (preferably native) from MOMP P5. Such replaced loops are most likely to adopt the native conformation of the loop 3 LB1(f) epitope within the altered outer membrane protein. Examples of entire loop 3s are shown in SEQ ID NO: 5-8. They may readily be determined by a skilled man by comparing a MOMP P5 sequence with the topology model of FIG. 2. Modified loops are preferably 13-75 amino acids long, more preferably 15-50, still more preferably 20-40, and most preferably about 30 amino acids long.

The LB1 (f) peptides relate to the representative peptides of Groups 1, 2a, 2b, and 3 (SEQ ID NO: 1, 2, 4, and 3 respectively, comprised within the entire loop 3 sequences of SEQ ID NO: 5, 6, 8, and 7 respectively), and to antigenically related variants of these peptides (or entire loop 3 sequences). "Antigenically related variants" can be either natural variants (as exemplified by the peptides disclosed in WO 99/64067) or artificially modified variants that immunologically mimic the LB1(f) antigenic determinant site of the MOMP P5 protein. The antigenically related variants of the peptides should have an amino acid sequence identity of at least 75% to one of the peptides provided in SEQ ID NO:1-8 (and more preferably at least 85%, and most preferably at least 95% identity), whilst still being capable of immunologically mimicking the corresponding antigenic determinant site of the MOMP P5 of non-typeable *Haemophilus influenzae*. For this invention "immunologically mimicking the corresponding antigenic determinant site of the MOMP P5 of ntHi" is defined as a (variant) peptide (or entire loop 3) inserted or replaced into a loop of an outer membrane protein being capable of inducing antibodies that specifically recognises one of the wild-type LB1(f) sequences (listed in tables 2, 3, and 4 of WO 99/64067) in the context of its natural environment within MOMP P5 AND/OR defined as a (variant) peptide (or entire loop 3) inserted or replaced into a loop of an outer membrane protein being capable of being recognised by the same immunospecific antibody that recognises one of the wild-type LB1(f) sequences (listed in tables 2, 3, and 4 of WO 99/64067) in its natural context within the MOMP-P5 protein. Preferably, the recognition test used above is that one sequence (wild-type or variant) has more than 30, 40, 50, 60, 70, 80, 90% of the avidity of the other sequence (variant or wild-type, respectively) in an ELISA test using the antibodies as defined above. Most preferably, the variant sequence is approximately equivalent to the wild-type sequence in terms of being able to protect a host against non-typeable *H. influenzae*.

Antigenically related variants may have had amino acids added, inserted, substituted or deleted. Preferred variants are those that differ from the referents by conservative (preferably single) amino acid substitutions.

Such peptide insertions and replacements can be achieved by the skilled person using standard, well-known molecular biology techniques (see for example the standard textbook Sambrook et al. "Molecular Cloning a Laboratory Manual"

(1989) Cold Spring Harbor Laboratory Press). In particular, knowing the DNA sequence of the native outer membrane protein target, primers may be straightforwardly designed to replace a nucleotide sequence encoding a native loop sequence with a nucleotide sequence encoding a modified loop sequence by PCR.

In a preferred embodiment, the native outer membrane protein target is MOMP P5 itself. The sequences of loops 1, 2, 3 and 4 can be seen in FIG. 2. Surprisingly, the modified MOMP P5 proteins of the invention have one or more of the following advantages: the LB1(f) peptides are located in a more favourable location for assuming a natural conformation for an optimal immune response effective against the peptide in its natural environment; highly variable, non-protective loop structures (within loops 1, 2 and 4) may be removed to focus the immune response away from these epitopes; a single, immunogenic MOMP P5 molecule can be made that can provide a host with protective immunity against a wide range of ntHi strains; the clustering of the LB1 (f) peptides on different loops of a single molecule provides a synergistic improvement of the immune response of a host against a wide range of ntHi strains.

Preferably the third loop of the protein is left unchanged. This is advantageous due to this loop already carrying an LB1(f) peptide in a native conformation.

Preferably, the modified MOMP P5 protein has had one or more of (preferably all of) loops 1, 2 and 4 replaced with a modified loop comprising a different Group 1, 2a, 2b or 3 LB1(f) peptide (in any order), which is also from a different Group to the LB1(f) peptide retained on loop 3. For instance, if the loop 3 peptide is from group 3, native loops 1, 2 and 4 can be replaced with a modified loop comprising a Group 1, 2a and 2b peptide, respectively (or in fact in any order), or antigenically related variants thereof. Preferably the LB1(f) peptides are selected from the group SEQ ID NO: 1-4 (containing a representative from each group of peptides). If an entire native loop is replaced with an entire loop 3 sequence, preferably the loop 3 sequences are selected from the group SEQ ID NO: 5-8 (containing a representative from each LB1 (f) Group).

Alternatively, the modified MOMP P5 protein has had one or more of (preferably both of) loops 1 and 2 replaced with a modified loop comprising a different Group 1, 2a, 2b or 3 LB1(f) peptide (in any order), which is also from a different Group to the LB1(f) peptide retained on loop 3, and loop 4 is replaced with a modified loop comprising a further *H. influenzae* protective epitope. Such further epitope is preferably the peptide from loop 5 or 6 of MOMP P2 from ntHi. Preferably the entire loop 4 is replaced with a modified loop which is the entire loop 5 or 6 MOMP P2 peptide sequence (topology models for MOMP P2 clearly defining the loop regions are known in the art: Kyungcheol and Murphy (1997) Infect. Immun. 65:150; Neary et al. (1999) 99th Gen. meeting of the ASM, Poster E-10; Duim et al. (1996) Infect. Immun. 64:4673). Preferably the LB1(f) peptides are selected from the group SEQ ID NO: 1-4. If an entire native loop is replaced with an entire loop 3 sequence, preferably the loop 3 sequences are selected from the group SEQ ID NO: 5-8 (containing a representative from each LB1(f) Group).

Furthermore, truncations of the MOMP P5 proteins of the invention which still have all 4 loop regions intact are also considered to be proteins of the invention.

Polynucleotides of the Invention

A further aspect of the invention is a DNA or RNA molecule encoding a recombinant outer membrane protein of the invention. In establishing this, the degeneracy of codon usage is relevant. Preferably codons well known to be optimal for expression in different expression hosts should be utilised. Preferably the LB1 (f) peptide-encoding nucleotides are of the same sequence as the wild-type sequences provided in Tables 6-8 of WO 99/64067.

The invention also provides polynucleotides which are complementary to all the above described polynucleotides.

When the polynucleotides of the invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821-824, or is an HA tag, or is glutathione-s-transferase. The polynucleotide may also contain non-coding 5' and 3' sequences, such as transcribed, non-translated sequences, splicing and polyadenylation signals, ribosome binding sites and sequences that stabilize mRNA.

Vectors, Host Cells, Expression

Still further aspects of the invention are an expression vector comprising the DNA or RNA molecule of the invention, wherein said expression vector is capable of expressing a recombinant outer membrane protein of the invention when present in a compatible host cell, and a host cell comprising this expression vector.

An alternative embodiment is a recombinant host containing the DNA or RNA molecule of the invention within its chromosome (which may be readily integrated by well known techniques such as homologous recombination using a known nucleotide sequence on the genome), wherein said molecule is in a context suitable for expressing a recombinant outer membrane protein of the invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING. A LABORATORY MANUAL,* 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as meningococci, streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells. Where the DNA molecule of the invention is integrated into the genome of the host cell, preferably the host is ntHi or *Moraxella catarrhalis*.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaceinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

Purification of Recombinantly Expressed Peptides/Polypeptides

A still further aspect of the invention is a process for producing a recombinant outer membrane protein of the invention comprising culturing the host cell (either containing the DNA molecule of the invention within an expression vector, or integrated into its chromosome) under conditions sufficient for the production of said protein, and recovering the recombinant outer membrane protein. The protein may be recovered as a purified product. The protein may also be recovered within a bleb (outer membrane vesicle) preparation that may be generated from the host cell (particularly where it is a Gram negative bacterium—preferably ntHi or *M catarrhalis*) using known techniques. The protein may be recovered within a ghost (outer membrane) preparation that may be generated from the host cell (particularly where it is a Gram negative bacterium—preferably ntHi) using known techniques (see WO 92/01791). Lastly, the protein may be recovered within a killed, live, or live-attenuated whole cell preparation from the host bacterium.

It is within the common general knowledge of the skilled person how to isolate outer membrane vesicles or ghosts from a host which would contain the protein of the invention. The advantage of such techniques is that the recombinant outer membrane protein of the invention remains properly folded within the vesicles and thus presents its native conformation to the immune system if used as a immunogen.

Proteins of the invention can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Well known techniques for refolding proteins may be employed to regenerate active conformation when the polypeptide is denatured during isolation and or purification.

Although the gene sequence of the chimeric LB1 (f) polypeptide in the vector can be tagged with a Histidine-tag sequence which aids the purification of the polypeptide, it is not an essential element to the invention, as polypeptides without the Histidine-tag can still be purified by one of the techniques mentioned above.

Vaccines

A further aspect of the invention is a vaccine composition (or an immunogenic composition) comprising an immunogenic amount (preferably an effective or protective amount) of the recombinant outer membrane protein of the invention (either isolated or purified, or present in a outer membrane vesicle, ghost or killed, live, or live-attenuated whole cell preparation) in a pharmaceutically acceptable excipient, and an optional adjuvant. In this context, immunogenic amount is defined as a sufficient quantity of protein to elicit an antibody response in a host vaccinee.

Still further aspects of the invention are: the use of an immunogenic amount of the recombinant outer membrane protein of the invention in a pharmaceutically acceptable excipient, and an optional adjuvant, to prevent or treat *Haemophilus influenzae* disease (preferably otitis media, sinusitis, conjunctivitis, or lower respiratory tract infection); a method of inducing an immune response in a mammal susceptible to *Haemophilus influenzae* infection comprising the administration to the mammal of an effective amount of the aforementioned vaccine (an effective amount being an amount capable of protecting a host [for instance chinchilla] to some degree against an ntHi infection); and a method of preventing *Haemophilus influenzae* infection comprising the administration to a mammal an effective amount of a vaccine of the invention.

Vaccines of the invention are capable of eliciting a cross-protective immune response against a large variety of ntHi strains (particularly where one or more modified loops are integrated into a ntHi outer membrane protein).

A preferred vaccine of the invention comprises a modified *M. catarrhalis* outer membrane protein comprising one or more modified loop regions, as such preparations may more effectively protect a host against otitis media by immunisation with a single molecule.

Vaccine preparation is generally described in Vaccine Design ("The subunit and adjuvant approach" (eds. Powell M. F. & Newman M. J). (1995) Plenum Press New York).

Additionally, the proteins of the present invention are preferably adjuvanted in the vaccine formulation of the invention. Suitable adjuvants include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatised polysaccharides, or polyphosphazenes. Other known adjuvants include CpG containing oligonucleotides. The oligonucleotides are characterised in that the CpG dinucleotide is unmethylated. Such oligonucleotides are well known and are described in, for example WO96/02555.

Further preferred adjuvants are those which induce an immune response preferentially of the TH1 type. High levels of Th1-type cytokines tend to favour the induction of cell mediated immune responses to the given antigen, whilst high levels of Th2-type cytokines tend to favour the induction of humoral immune responses to the antigen. Suitable adjuvant systems include, for example monophosphoryl lipid A, preferably 3-de-O-acylated monophosphoryl lipid A (3D-MPL), or a combination of 3D-MPL together with an aluminium salt. CpG oligonucleotides also preferentially induce a TH1 response. An enhanced system involves the combination of a monophosphoryl lipid A and a saponin derivative particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21 3D-MPL & tocopherol in an oil in water emulsion is described in WO 95/17210 and is a preferred formulation.

The vaccine composition of the invention is preferably administered orally, intranasally or parenterally (including subcutaneous, intramuscular, intravenous, intradermal, transdermal injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant as described above. The dosage will depend on the specific activity of the vaccine and can be readily determined by routine experimentation. It should be an amount which induces an immunoprotective response without significant, adverse side effects in typical vaccinees (typically 1-100 µg of protein antigen, preferably 5-50 µg, and most typically in the range 5-25 µg).

Yet another aspect relates to an immunological/vaccine formulation which comprises the polynucleotide of the invention. Such techniques are known in the art, see for example Wolff et al., Science, (1990) 247: 1465-8.

The proteins of this invention can be administered as multivalent subunit vaccines in combination with antigens from other proteins of *H. influenzae* to achieve an enhanced bactericidal activity. They can also be administered in combination with polysaccharide antigens, for example the PRP capsular polysaccharide (preferably conjugated to a protein such as tetanus toxoid) of *H. influenzae* b. For combined administration with epitopes of other proteins, the protein of the invention is either administered separately, as a mixture (for instance within a outer membrane vesicle preparation) or as a conjugate or genetic fusion polypeptide. The conjugate is formed by standard techniques for coupling proteinaceous materials. The proteins of the invention can be used in conjunction with antigens of other organisms (e.g. encapsulated or nonencapsulated, bacteria, viruses, fungi and parasites). For example, the proteins of the invention are useful in conjunction with antigens of other microorganisms implicated in otitis media or other diseases. These include *Streptococcus pneumoniae, Streptococcus* pyrogenes group A, *Staphylococcus aureus*, respiratory syncytial virus and *Moraxella catarrhalis*.

The evaluation of the proteins of the invention as potential vaccines against ntHi-caused otitis media can be made in a chinchilla animal model (WO 99/64067). This model mimics the development of otitis media in children and is based on the successive intranasal administrations of adenovirus and ntHi a week apart. In these conditions, the bacteria is able, after the colonisation of the nasopharynx, to invade the middle ear via the Eustachian tube. Once there, ntHi will proliferate and induce an inflammatory process similar to what is observed in children.

For vaccine evaluation, by the time the chinchilla has been actively immunised they are too old at the time of challenge to be inoculated by the intranasal route with ntHi: even with a preinfection with adenovirus, almost none of them will develop otitis media. As an alternative route of challenge, a direct inoculation of the bacteria into the middle ear (bullae) through the skull is used. Passive transfer/challenge protocols can also be used to avoid needing trans-bullar challenge.

With all these types of challenge, the severity of the disease can be scored by otoscopic observation (through the external ear) or tympanometry, which evaluate the level of inflammation in the middle ear or changes in middle ear pressure and presence of fluid in the middle ear, respectively. The efficacy of a vaccine is determined by the reduction of the severity and/or the duration of the inflammation and the reduction of the colonisation in the ear and the nasopharynx.

The vaccines of the invention can be further evaluated by examining whether the proteins of the invention inhibit adherence of ntHi to chinchilla epithelial throat cells, and whether they can prevent nasopharyngeal colonisation by ntHi in vivo. Nasopharygeal colonisation is an initial step required for the development of otitis media, therefore this inhibition of colonisation will also help to inhibit the development of otitis media.

Cited documents are incorporated by reference herein.

```
                                                  SEQ ID NO: 1
RSDYKFYEDANGTRDHKKG
[from strain ntHi-1128 (Group 1 type)]

SEQ ID NO: 2
RSDYKLYNKNSSSNSTLKNLGE
[from strain ntHi-1715MEE (Group 2a type)]

SEQ ID NO: 3
RSDYKFYDNKRID
[(from strain ntHi-1729MEE (Group 3 type)]

SEQ ID NO: 4
RSDYKLYNKNSSTLKDLGE
[from strain ntHi-183NP (Group 2b type)]

SEQ ID NO: 5
LVRSDYKFYEDANGTRDHKKGRHTARAS
[entire third loop from strain ntHi-1128
(Group 1 type)]

SEQ ID NO: 6
LVRSDYKLYNKNSSSNSTLKNLGEHHRARAS
[entire third loop from strain ntHi-1715MEE
(Group 2a type)]

SEQ ID NO: 7
LVRSDYKFYDNKRIDSHRARAS
[entire third loop from strain ntHi-1729MEE
(Group 3 type)]

SEQ ID NO: 8
LVRSDYKLYNKNSSTLKDLGEHHRARAS
[entire third loop from strain ntHi-183NP
(Group 2b type)]
```

We claim:

1. A non-typeable *Haemophilus influenza* major outer membrane P5 chimeric protein comprising:
    a first region comprising amino acids 1 to 37 of SEQ ID NO: 9;
    a second region comprising a first loop selected from the group consisting of amino acids 38 to 57 of SEQ ID NO: 9, SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8;
    a third region comprising amino acids 58 to 88 of SEQ ID NO: 9;
    a fourth region comprising a second loop selected from the group consisting of amino acids 89 to 100 of SEQ ID NO: 9, SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8;
    a fifth region comprising amino acids 101 to 135 of SEQ ID NO: 9;

a sixth region comprising a third loop selected from the group consisting of amino acids 136 to 150 of SEQ ID NO: 9, SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8;

a seventh region comprising amino acids 151 to 180 of SEQ ID NO: 9;

an eighth region comprising a fourth loop selected from the group consisting of amino acids 181 to 204 of SEQ ID NO: 9, SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; and a ninth region comprising amino acids 205 to 353 of SEQ ID NO: 9, wherein at least one of the first, second, third, or fourth loops comprise an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8, and wherein the regions are covalently linked, respectively.

2. An immunogenic composition comprising an effective amount of the chimeric protein of claim 1.

3. A method of inducing an immune response in a mammal susceptible to *Haemophilus influenzae* infection comprising administration to the mammal of an effective amount of the immunogenic composition according to claim 2.

4. The chimeric protein of claim 1, wherein the sixth region comprising a third loop is selected from amino acids 136 to 150 of SEQ ID NO: 9.

5. The chimeric protein of claim 1, wherein:

the first region consists of amino acids 1 to 37 of SEQ ID NO: 9;

the third region consists of amino acids 58 to 88 of SEQ ID NO: 9;

the fifth region consists of amino acids 101 to 135 of SEQ ID NO: 9;

the seventh region consists of amino acids amino acids 151 to 180 of SEQ ID NO: 9; and the ninth region consists of amino acids 205 to 353 of SEQ ID NO: 9.

6. The chimeric protein of claim 5, wherein:

the second region consists of a first loop selected from the group consisting of amino acids 38 to 57 of SEQ ID NO: 9, SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8;

the fourth region consists of a second loop selected from the group consisting of amino acids 89 to 100 of SEQ ID NO: 9, SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8;

the sixth region consists of a third loop selected from the group consisting of amino acids 136 to 150 of SEQ ID NO: 9, SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; and the eighth region consists of a fourth loop selected from the group consisting of amino acids 181 to 204 of SEQ ID NO: 9, SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

7. The chimeric protein of claim 6, wherein the sixth region consists of a third loop selected from amino acids 136 to 150 of SEQ ID NO: 9.

8. The immunogenic composition of claim 2 further comprising a pharmaceutically acceptable excipient.

9. The immunogenic composition of claim 8 further comprising an adjuvant.

10. The method of claim 3 wherein the mammal is a human.

* * * * *

SEQUENCE LISTING

<160> NUMBER OF SEQ ID NOS: 10

<210> SEQ ID NO 1
<211> LENGTH: 19
<212> TYPE: PRT
<213> ORGANISM: Haemophilus influenzae

<400> SEQUENCE: 1

```
Arg Ser Asp Tyr Lys Phe Tyr Glu Asp Ala Asn Gly Thr Arg Asp His
1               5                   10                  15

Lys Lys Gly

<210> SEQ ID NO 2
<211> LENGTH: 22
<212> TYPE: PRT
<213> ORGANISM: Haemophilus influenzae

<400> SEQUENCE: 2

Arg Ser Asp Tyr Lys Leu Tyr Asn Lys Asn Ser Ser Ser Asn Ser Thr
1               5                   10                  15

Leu Lys Asn Leu Gly Glu
            20

<210> SEQ ID NO 3
<211> LENGTH: 13
<212> TYPE: PRT
<213> ORGANISM: Haemophilus influenzae

<400> SEQUENCE: 3

Arg Ser Asp Tyr Lys Phe Tyr Asp Asn Lys Arg Ile Asp
1               5                   10

<210> SEQ ID NO 4
<211> LENGTH: 19
<212> TYPE: PRT
<213> ORGANISM: Haemophilus influenzae

<400> SEQUENCE: 4

Arg Ser Asp Tyr Lys Leu Tyr Asn Lys Asn Ser Ser Thr Leu Lys Asp
1               5                   10                  15

Leu Gly Glu

<210> SEQ ID NO 5
<211> LENGTH: 28
<212> TYPE: PRT
<213> ORGANISM: Haemophilus influenzae

<400> SEQUENCE: 5

Leu Val Arg Ser Asp Tyr Lys Phe Tyr Glu Asp Ala Asn Gly Thr Arg
1               5                   10                  15

Asp His Lys Lys Gly Arg His Thr Ala Arg Ala Ser
            20                  25

<210> SEQ ID NO 6
<211> LENGTH: 31
<212> TYPE: PRT
<213> ORGANISM: Haemophilus influenzae

<400> SEQUENCE: 6

Leu Val Arg Ser Asp Tyr Lys Leu Tyr Asn Lys Asn Ser Ser Ser Asn
1               5                   10                  15

Ser Thr Leu Lys Asn Leu Gly Glu His His Arg Ala Arg Ala Ser
            20                  25                  30

<210> SEQ ID NO 7
<211> LENGTH: 22
<212> TYPE: PRT
<213> ORGANISM: Haemophilus influenzae

<400> SEQUENCE: 7
```

```
Leu Val Arg Ser Asp Tyr Lys Phe Tyr Asp Asn Lys Arg Ile Asp Ser
1               5                   10                  15

His Arg Ala Arg Ala Ser
            20

<210> SEQ ID NO 8
<211> LENGTH: 28
<212> TYPE: PRT
<213> ORGANISM: Haemophilus influenzae

<400> SEQUENCE: 8

Leu Val Arg Ser Asp Tyr Lys Leu Tyr Asn Lys Asn Ser Ser Thr Leu
1               5                   10                  15

Lys Asp Leu Gly Glu His His Arg Ala Arg Ala Ser
            20                  25

<210> SEQ ID NO 9
<211> LENGTH: 356
<212> TYPE: PRT
<213> ORGANISM: Haemophilus influenzae

<400> SEQUENCE: 9

Met Lys Lys Thr Ala Ile Ala Leu Val Val Ala Gly Leu Ala Ala Ala
1               5                   10                  15

Ser Val Ala Gln Ala Ala Pro Gln Glu Asn Thr Phe Tyr Ala Gly Val
            20                  25                  30

Lys Ala Gly Gln Ala Ser Phe His Asp Gly Leu Arg Ala Leu Ala Arg
        35                  40                  45

Glu Tyr Leu Lys Val Gly Tyr His Arg Asn Ser Phe Thr Tyr Gly Val
    50                  55                  60

Phe Gly Gly Tyr Gln Ile Leu Asn Gln Asn Asn Leu Gly Leu Ala Val
65                  70                  75                  80

Glu Leu Gly Tyr Asp Asp Phe Gly Arg Ala Lys Gly Arg Glu Lys Gly
                85                  90                  95

Lys Thr Val Val Lys Leu His Thr Asn His Gly Thr His Leu Ser Leu
            100                 105                 110

Lys Gly Ser Tyr Glu Val Leu Glu Gly Leu Asp Val Tyr Gly Lys Ala
        115                 120                 125

Gly Val Ala Leu Val Arg Ser Asp Tyr Lys Leu Tyr Asn Glu Asn Ser
    130                 135                 140

Ser Thr Leu Lys Lys Leu Gly Glu Leu His His Arg Ala Arg Ala Ser
145                 150                 155                 160

Gly Leu Phe Ala Val Gly Ala Glu Tyr Ala Val Leu Pro Glu Leu Ala
                165                 170                 175

Val Arg Leu Glu Tyr Gln Trp Leu Thr Arg Val Gly Lys Tyr Arg Pro
            180                 185                 190

Gln Asp Lys Pro Asn Thr Ala Leu Asn Tyr Asn Pro Trp Ile Gly Ser
        195                 200                 205

Ile Asn Ala Gly Ile Ser Tyr Arg Phe Gly Gln Gly Ala Ala Pro Val
    210                 215                 220

Val Ala Ala Pro Glu Val Val Ser Lys Thr Phe Ser Leu Asn Ser Asp
225                 230                 235                 240

Val Thr Phe Ala Phe Gly Lys Ala Asn Leu Lys Pro Gln Ala Gln Ala
                245                 250                 255

Thr Leu Asp Ser Ile Tyr Gly Glu Met Ser Gln Val Lys Ser Ala Lys
            260                 265                 270
```

```
Val Ala Val Ala Gly Tyr Thr Asp Arg Ile Gly Ser Asp Ala Phe Asn
        275             280             285

Val Lys Leu Ser Gln Glu Arg Ala Asp Ser Val Ala Asn Tyr Phe Val
        290             295             300

Ala Lys Gly Val Ala Ala Asp Ala Ile Ser Ala Thr Gly Tyr Gly Lys
305             310             315             320

Ala Asn Pro Val Thr Gly Ala Thr Cys Asp Gln Val Lys Gly Arg Lys
                325             330             335

Ala Leu Ile Ala Cys Phe Ala Pro Asp Arg Arg Val Glu Ile Ala Val
                340             345             350

Asn Gly Thr Lys
        355

<210> SEQ ID NO 10
<211> LENGTH: 200
<212> TYPE: PRT
<213> ORGANISM: Haemophilus influenzae

<400> SEQUENCE: 10

Ala Pro Gln Glu Asn Thr Phe Tyr Ala Gly Val Lys Ala Gly Gln Ala
1               5                   10                  15

Ser Phe His Asp Gly Ile Asn Asn Gly Ala Ile Lys Lys Gly Leu
                20                  25                  30

Ser Ser Ser Asn Tyr Gly Tyr Arg Arg Asn Thr Phe Thr Tyr Gly Val
            35                  40                  45

Phe Gly Gly Tyr Gln Ile Leu Asn Gln Asp Asn Phe Gly Leu Ala Ala
        50                  55                  60

Glu Leu Gly Tyr His Asp Phe Gly Arg Ala Lys Leu Arg Glu Ala Gly
65                  70                  75                  80

Lys Pro Lys Ala Lys His Thr Asn His Gly Ala Tyr Leu Ser Leu Lys
                85                  90                  95

Gly Ser Tyr Glu Val Leu Glu Gly Leu Asp Val Tyr Gly Lys Ala Gly
            100                 105                 110

Val Ala Leu Val Arg Ser Asp Tyr Lys Phe Tyr Glu Asp Ala Asn Gly
        115                 120                 125

Thr Arg Asp His Lys Lys Gly Arg His Thr Ala Arg Ala Ser Gly Leu
    130                 135                 140

Phe Ala Val Gly Ala Glu Tyr Ala Val Leu Pro Glu Leu Ala Val Arg
145                 150                 155                 160

Leu Glu Tyr Gln Trp Leu Thr Arg Val Gly Lys Tyr Arg Pro Gln Asp
                165                 170                 175

Lys Pro Asn Thr Ala Ile Asn Tyr Asn Pro Trp Ile Gly Cys Ile Asn
            180                 185                 190

Ala Gly Ile Ser Tyr Arg Phe Gly
        195                 200
```